United States Patent [19]

Clough et al.

[11] Patent Number: 5,374,644
[45] Date of Patent: Dec. 20, 1994

[54] FUNGICIDES

[75] Inventors: John M. Clough, Buckinghamshire; Christopher R. A. Godfrey, Bracknell; Ian T. Streeting, Wokingham, all of England

[73] Assignee: Imperial Chemical Industries PLC, London, England

[21] Appl. No.: 815,588

[22] Filed: Dec. 31, 1991

Related U.S. Application Data

[63] Continuation of Ser. No. 76,930, Jul. 23, 1987, abandoned.

[30] Foreign Application Priority Data

Aug. 6, 1986 [GB] United Kingdom ............... 8619236

[51] Int. Cl.$^5$ .................... C03D 263/58; A01N 43/76
[52] U.S. Cl. ..................... 514/375; 514/301; 514/354; 514/363; 514/367; 514/369; 514/372; 514/373; 514/376; 514/379; 514/380; 514/381; 514/384; 514/398; 514/407; 514/419; 514/424; 514/443; 514/445; 514/470; 514/473; 549/53; 549/63; 549/66; 549/466; 549/479
[58] Field of Search ............... 548/221, 226, 228, 229, 548/136, 170, 184, 187, 209, 13, 241, 243, 253, 255, 264.4, 319.5, 361.5, 366.1, 484, 486, 541, 551; 546/114, 53, 63, 66, 466, 479; 514/375, 301, 359, 363, 367, 364, 372, 373, 376, 379, 380, 381, 384, 398, 407, 419, 424, 443, 445, 47, 473

[56] References Cited

U.S. PATENT DOCUMENTS 4,468,244 8/1984 Krass ..................... 71/88
4,482,373 11/1984 Handte ................... 74/8.8

FOREIGN PATENT DOCUMENTS 178826 4/1986 European Pat. Off. ........... 548/200

Primary Examiner—Robert Gerstl
Attorney, Agent, or Firm—Cushman, Darby & Cushman

[57] ABSTRACT

Compounds of formula:

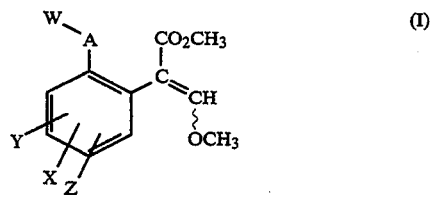

and stereoisomers thereof, wherein X, Y and Z, which are the same or different, are hydrogen, halogen, hydroxy, optionally substituted alkyl, optionally substituted alkenyl, optionally substituted aryl, optionally substituted alkynyl, optionally substituted alkoxy, optionally substituted aryloxy, optionally substituted aralkyl, optionally substituted arylalkoxy, optionally substituted aryloxyalkyl, optionally substituted acyloxy, optionally substituted amino, acylamino, nitro, cyano, $-CO_2R^1$, $-CONR^2R^3$, or $-COR^4$; or X and Y, when they are in adjacent positions of the phenyl ring, join to form a fused ring, either aromatic or aliphatic, optionally containing one or more heteroatoms; W is a C-linked optionally substituted five membered heterocylic ring, containing one to four hetero-atoms, which are the same or different, and which are nitrogen, sulphur or oxygen and wherein adjacent substituents may together form a fused aromatic or hetero-aromatic ring; A is an oxygen or sulphur atom; and $R^1$, $R^2$, $R^3$ and $R^4$, which are the same or different, are hydrogen, alkyl, cycloalkyl, cycloalkylalkyl, alkenyl, alkynyl, optionally substituted aryl or optionally substituted aralkyl; and metal complexes thereof. The compounds are useful as fungicides and also insecticides.

8 Claims, No Drawings

FUNGICIDES

This is a continuation of application Ser. No. 07/076,930, filed on Jul. 23, 1987, now abandoned.

This invention relates to derivatives of acrylic acid useful in agriculture (especially as fungicides but also as insecticides, nematicides and miticides), to processes for preparing them, to agricultural (especially fungicidal) compositions containing them, and to methods of using them to combat fungi, (especially fungal infections in plants) and to control or kill insect, nematode and mite pests.

The invention provides a compound having the general formula (I):

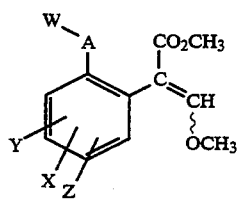

(I)

and stereoisomers thereof, wherein X, Y and Z, which are the same or different, are hydrogen, halogen, hydroxy, optionally substituted alkyl, optionally substituted alkenyl, optionally substituted aryl, optionally substituted alkynyl, optionally substituted alkoxy, optionally substituted aryloxy, optionally substituted aralkyl, optionally substituted arylalkoxy, optionally substituted aryloxyalkyl, optionally substituted acyloxy, optionally substituted amino, acylamino, nitro, cyano, $-CO_2R^1$, $-CONR^2R^3$, or $-COR^4$, or X and Y, when they are in adjacent positions on the phenyl ring, join to form a fused ring, either aromatic or aliphatic, optionally containing one or more heteroatoms; W is a C-linked optionally substituted five membered heterocyclic ring, containing one to four hetero-atoms, which are the same or different and which are nitrogen, sulphur or oxygen and wherein adjacent substituents may together form a fused aromatic or hetero-aromatic ring; A is an oxygen or sulphur atom; and $R^1$, $R^2$, $R^3$, and $R^4$, which are the same or different, are hydrogen atoms or alkyl, cycloalkyl, cycloalkylalkyl, alkenyl, alkynyl, optionally substituted aryl or optionally substituted aralkyl; and metal complexes thereof.

The compounds of the invention contain at least one carbon-carbon double bond, and are sometimes obtained in the form of mixtures of geometric isomers. However, these mixtures can be separated into individual isomers, and this invention embraces such isomers and mixtures thereof in all proportions including those which consist substantially of the (Z)-isomer and those which consist substantially of the (E)-isomer.

The individual isomers which result from the unsymmetrically substituted double bond of the acrylate group are identified by the commonly used terms "(E)" and "(Z)". These terms are defined according to the Cahn-Ingold-Prelog system which is fully described in the literature (see, for example, J March, "*Advanced Organic Chemistry*," 3rd edition, Wiley-Interscience, page 109 et seq).

Usually one isomer is more fungicidally active than the other; the more active isomer being the one in which the group $-OCH_3$ is on the same side of the double bond as the substituted phenyl ring. In the case of the compounds of the present invention this is the (E)-isomer. These isomers form a preferred embodiment of the invention.

The formula:

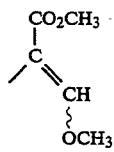

used hereinafter signifies a separable mixture of both geometric isomers about the acrylate double bond, i.e.

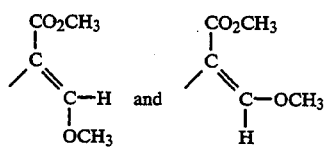

Alkyl, wherever present as a group or moiety (in, for example, "alkoxy" and "aralkyl") can be in the form of straight or branched chains, and preferably contains 1 to 6, more preferably 1 to 4, carbon atoms; examples are methyl, ethyl, propyl, (n- or iso-propyl) and butyl (n-, sec-, iso- or t-butyl). Optional substituents of alkyl include hydroxy, halogen (especially chlorine and fluorine), $C_{1-4}$ alkoxy and $C_{1-4}$ alkoxycarbonyl.

Preferred substituent haloalkyl groups are halo-($C_{1-4}$)alkyl groups and the same applies for preferred haloalkoxy groups. Of particular interest are trifluoromethyl and trifluoromethoxy. Cycloalkyl is preferably $C_{3-6}$ cycloalkyl and includes cyclohexyl. Cycloalkylalkyl is preferably $C_{3-6}$ cycloalkyl($C_{1-4}$)alkyl, for example, cyclopropylethyl.

Aralkyl itself and the aralkyl moiety of arylalkoxy include, particularly, phenylalkyl (especially benzyl, phenylethyl, phenylpropyl, phenylbutyl or phenylhexyl) in which the alkyl moiety may carry other substituents such as hydroxy or $C_{1-4}$ alkoxy and the aryl moiety may be substituted with, for example, one or more of halogen (especially chlorine or fluorine), hydroxy, $C_{1-4}$ alkyl (especially methyl), $C_{1-4}$ alkoxy (especially methoxy), trifluoromethyl, trifluoromethoxy, optionally substituted phenoxy, optionally substituted benzyloxy, nitro, amino, phenyl, carboxy or a carboxylic acid ester, cyano, alkylcarbonylamino and methylenedioxy. Substituents which may be present on the phenoxy and benzyloxy groups include any of those other substituents which may be present on the aryl moiety of aralkyl.

Aryloxyalkyl includes, in particular, phenoxyalkyl (especially phenoxymethyl and phenoxyethyl) in which the alkyl moiety may carry other substitutents such as methoxy and the aryl moiety may be substituted in the same way as the aryl moiety in aralkyl above.

Alkenyl and alkynyl groups preferably contain 2 to 6 carbon atoms and, more preferably, 2 to 4 carbon atoms in the form of straight or branched chains. Ethenyl, propenyl and butenyl are examples of alkenyl groups. Optional substituents or alkenyl include aromatic and heteroaromatic groups (such as phenyl, furyl, thienyl and pyridyl) which may themselves carry substituents such as those described for the aryl moiety of aralkyl above. These include halogen (especially chlorine or fluorine) Further, the terminal carbon atom of the alkenyl groups may form part of a 5- or 6-membered cycloalkyl ring. Alkynyl includes ethynyl and is optionally substituted by, for example, phenyl which may itself be substituted as for the aryl moiety of aralkyl above.

Aryl itself and the aryl moiety of aryloxy are preferably phenyl. They may be substituted in the same way as the aryl moiety of aralkyl above.

Optional substitutents which may be carried by an amino group include one or two of N-aryl and N-alkyl groups (such as N-phenyl or N-methyl).

Acyl itself and the acyl moiety of acyloxy include, in particular, acetyl and benzoyl in which the benzene ring may be substituted in the same way as the aryl moiety in aralkyl above. Acylamino includes benzoylamino, furoylamino and thienylcarbonylamino optionally substituted by, for example, N-alkyl (especially N-methyl).

Heterocyclic groups which W may be include furyl, thienyl, pyrrolyl, benzofuryl, benzothienyl, indolyl, pyrazolyl, isoxazolyl, isothiazolyl, oxazolyl, thiazolyl, imidazolyl, benzisoxazolyl, benzisothiazolyl, benzpyrazolyl, benzoxazolyl, benzthiazolyl, 1,2,3-triazolyl, 1,2,4-triazolyl, tetrazolyl and thiazolo[5,4-b]pyrid-2-yl. The foregoing may bear one or more ring substituents or, in the case of a fused ring system may bear one or more substituents on either, or both, rings. Examples of such substituents are halogen nitro, $C_{1-4}$ alkyl, optionally substituted with halogen, hydroxy or $C_{1-4}$ alkoxy, $C_{1-4}$ alkoxy optionally substituted with halogen, hydroxy or $C_{1-4}$ alkoxy, phenoxy optionally substituted with halogen, amino optionally substituted with $C_{1-4}$ alkyl, or cyano.

In a preferred aspect of the invention the group W has the formula (A):

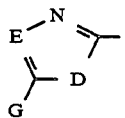
(A)

in which D is O or S; E is N or C-J and G and J are independently hydrogen, halogen (especially bromine, chlorine or fluorine), hydroxy, $C_{1-4}$ alkyl, $C_{1-4}$ alkoxy, halo($C_{1-4}$)alkyl (especially trifluoromethyl), halo($C_{1-4}$)alkoxy (especially trifluoromethoxy), phenoxy, nitro, amino or mono- or di-($C_{1-4}$)alkylamino; or G and J join to form a fused optionally substituted 5- or 6-membered ring, either aliphatic or aromatic, optionally containing one or more heteroatoms.

Optional substituents carried by the fused ring formed by G and J include those substituents given for G and J above.

Preferred fused rings formed by G and J are benzene, pyridine and pyrimidine rings.

Examples of the group

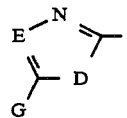

are benzoxaloyl, benzthiazolyl, thiazolopyridyl, thiazolyl and 1,3,4-thiadiazolyl optionally carrying one or more of the substituents given for G and J above.

With all values of W it is preferred that X, Y and Z, which are the same or different, are single atoms or sterically small groups such as fluoro, chloro, bromo, hydroxy, methyl, methoxy, trifluoromethyl, methylamino or dimethylamino but are preferably hydrogen.

A is preferably oxygen.

The invention is illustrated by the compounds presented in Table I below.

TABLE I

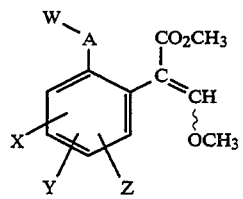

| Compound No. | W | A | X | Y | Z | Melting Point (°C.) | Olefinic* | Isomer+ |
| --- | --- | --- | --- | --- | --- | --- | --- | --- |
| 1 | 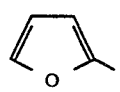 | O | H | H | H | | | E |
| 2 | 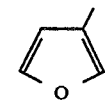 | O | H | H | H | | | E |
| 3 | 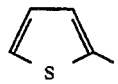 | O | H | H | H | | | E |

TABLE I-continued

Structure:
- Central benzene ring with substituents W-A at one position and C(=CH-OCH₃)(CO₂CH₃) at adjacent position
- X, Y, Z positions on benzene ring

| Compound No. | W | A | X | Y | Z | Melting Point (°C.) | Olefinic* | Isomer+ |
|---|---|---|---|---|---|---|---|---|
| 4 | 3-chloro-5-methyl-thienyl (Cl on thiophene, S) | O | H | H | H | | | E |
| 5 | 5-chloro-thienyl (Cl-S) | O | H | H | H | | | E |
| 6 | 5-bromo-thienyl (Br-S) | O | H | H | H | | | E |
| 7 | 5-nitro-thienyl (NO₂-S) | O | H | H | H | | | E |
| 8 | 3-thienyl (S) | O | H | H | H | | | E |
| 9 | 2-chloro-4-methyl-thienyl (Cl, S) | O | H | H | H | | | E |
| 10 | 2-bromo-4-methyl-thienyl (Br, S) | O | H | H | H | | | E |
| 11 | N-methyl-pyrrolyl (N-Me) | O | H | H | H | | | E |
| 12 | N-methyl-pyrrolyl (N-Me) | O | H | H | H | | | E |
| 13 | benzofuran-2-yl (O) | O | H | H | H | | | E |
| 14 | benzofuran-3-yl (O) | O | H | H | H | | | E |

TABLE I-continued

| Compound No. | W | A | X | Y | Z | Melting Point (°C.) | Olefinic* | Isomer+ |
|---|---|---|---|---|---|---|---|---|
| 15 | 2-benzothiophenyl | O | H | H | H | | | E |
| 16 | 3-benzothiophenyl | O | H | H | H | | | E |
| 17 | 3-pyrrolyl (NH) | O | H | H | H | | | E |
| 18 | 2-pyrrolyl (NH) | O | H | H | H | | | E |
| 19 | 3-indolyl (NH) | O | H | H | H | | | E |
| 20 | 2-indolyl (NH) | O | H | H | H | | | E |
| 21 | 3-indolyl (N-Me) | O | H | H | H | | | E |
| 22 | 2-indolyl (N-Me) | O | H | H | H | | | E |
| 23 | 4-(1-methylpyrazolyl) | O | H | H | H | | | E |

TABLE I-continued

[Structure: benzene ring with W-A substituent, C(CO2CH3)=CH-OCH3 group, and X, Y, Z substituents]

| Compound No. | W | A | X | Y | Z | Melting Point (°C.) | Olefinic* | Isomer+ |
|---|---|---|---|---|---|---|---|---|
| 24 | 3-methyl-1-methylpyrazol-5-yl (N—N-Me) | O | H | H | H | | | E |
| 25 | 5-methyl-1-methylpyrazol-3-yl (N—N-Me) | O | H | H | H | | | E |
| 26 | 3-methylisoxazol-5-yl | O | H | H | H | | | E |
| 27 | 4-methylisoxazol-5-yl | O | H | H | H | | | E |
| 28 | 5-methylisoxazol-3-yl | O | H | H | H | | | E |
| 29 | 3-methylisothiazol-5-yl | O | H | H | H | | | E |
| 30 | 4-methylisothiazol-5-yl | O | H | H | H | | | E |
| 31 | 5-methylisothiazol-3-yl | O | H | H | H | | | E |
| 32 | 4-methyloxazolin-2-yl | O | H | H | H | | | E |
| 33 | 4-methyloxazol-2-yl | O | H | H | H | | | E |
| 34 | oxazol-2-yl | O | H | H | H | | | E |

TABLE I-continued

| Compound No. | W | A | X | Y | Z | Melting Point (°C.) | Olefinic* | Isomer+ |
|---|---|---|---|---|---|---|---|---|
| 35 | 4-methylthiazol-5-yl | O | H | H | H | | | E |
| 36 | 5-methylthiazol-4-yl | O | H | H | H | | | E |
| 37 | 2-methylthiazol-? | O | H | H | H | | | E |
| 38 | 1-methyl-5-methylimidazol-4-yl | O | H | H | H | | | E |
| 39 | 1-methyl-4-methylimidazol-5-yl | O | H | H | H | | | E |
| 40 | 1-methyl-2-methylimidazol-? | O | H | H | H | | | E |
| 41 | benzisoxazol-3-yl | O | H | H | H | | | E |
| 42 | benzisothiazol-3-yl | O | H | H | H | | | E |
| 43 | 1-methylindazol-3-yl | O | H | H | H | | | E |
| 44 | benzoxazol-2-yl | O | H | H | H | 89–90 | 7.80 | E |

TABLE I-continued

| Compound No. | W | A | X | Y | Z | Melting Point (°C.) | Olefinic* | Isomer+ |
|---|---|---|---|---|---|---|---|---|
| 45 | 5-Cl-benzoxazol-2-yl | O | H | H | H | 129–131 | 7.54 | E |
| 46 | 6-F-benzoxazol-2-yl | O | H | H | H | 94–5 | 7.54 | E |
| 47 | benzothiazol-2-yl | O | H | H | H | | | E |
| 48 | 5-F-benzothiazol-2-yl | O | H | H | H | | | E |
| 49 | 6-F-benzothiazol-2-yl | O | H | H | H | | | E |
| 50 | thiazolo[5,4-b]pyridin-2-yl | O | H | H | H | 109–111 | 7.53 | E |
| 51 | 6-Cl-thiazolo[5,4-b]pyridin-2-yl | O | H | H | H | 113–114 | 7.52 | E |
| 52 | 1-methyl-1H-tetrazol-5-yl (isomer a) | O | H | H | H | | | E |
| 53 | 1-methyl-1H-tetrazol-5-yl (isomer b) | O | H | H | H | | | E |
| 54 | 1-methyl-1H-1,2,4-triazol-5-yl | O | H | H | H | | | E |
| 55 | 1-methyl-1H-1,2,4-triazol-3-yl | O | H | H | H | | | E |

TABLE I-continued
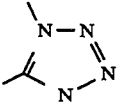
| Compound No. | W | A | X | Y | Z | Melting Point (°C.) | Olefinic* | Isomer+ |
|---|---|---|---|---|---|---|---|---|
| 56 | 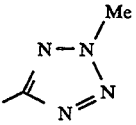 | O | H | H | H | | | E |
| 57 | 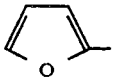 | O | H | H | H | | | E |
| 58 | 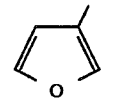 | S | H | H | H | | | E |
| 59 | 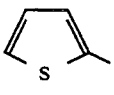 | S | H | H | H | | | E |
| 60 | 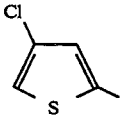 | S | H | H | H | | | E |
| 61 | 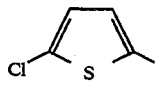 | S | H | H | H | | | E |
| 62 | 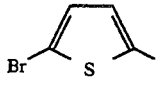 | S | H | H | H | | | E |
| 63 | 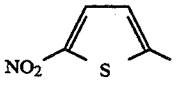 | S | H | H | H | | | E |
| 64 | 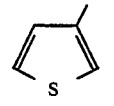 | S | H | H | H | | | E |
| 65 | 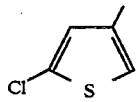 | S | H | H | H | | | E |
| 66 |  | S | H | H | H | | | E |

TABLE I-continued
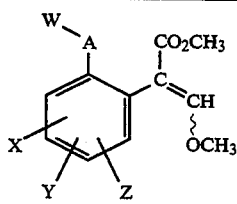
| Compound No. | W | A | X | Y | Z | Melting Point (°C.) | Olefinic* | Isomer+ |
|---|---|---|---|---|---|---|---|---|
| 67 | 2-bromo-4-methylthiophene | S | H | H | H | | | E |
| 68 | 3-methyl-N-methylpyrrole | S | H | H | H | | | E |
| 69 | 2-methyl-N-methylpyrrole | S | H | H | H | | | E |
| 70 | 2-benzofuranyl | S | H | H | H | | | E |
| 71 | 3-benzofuranyl | S | H | H | H | | | E |
| 72 | 2-benzothienyl | S | H | H | H | | | E |
| 73 | 3-benzothienyl | S | H | H | H | | | E |
| 74 | 3-methylpyrrole | S | H | H | H | | | E |
| 75 | 2-methylpyrrole | S | H | H | H | | | E |

TABLE I-continued

Structure:

W–A attached to benzene ring bearing substituents X, Y, Z, with side chain C(CO$_2$CH$_3$)=CH–OCH$_3$

| Compound No. | W | A | X | Y | Z | Melting Point (°C.) | Olefinic* | Isomer+ |
|---|---|---|---|---|---|---|---|---|
| 76 | 3-indolyl (NH) | S | H | H | H | | | E |
| 77 | 2-indolyl (NH) | S | H | H | H | | | E |
| 78 | 3-indolyl (N-Me) | S | H | H | H | | | E |
| 79 | 2-indolyl (N-Me) | S | H | H | H | | | E |
| 80 | 4-methyl-1-methylpyrazolyl | S | H | H | H | | | E |
| 81 | 3-methyl-1-methylpyrazolyl | S | H | H | H | | | E |
| 82 | 3-methyl-1-methylpyrazolyl (isomer) | S | H | H | H | | | E |
| 83 | 3-methylisoxazolyl | S | H | H | H | | | E |
| 84 | 4-methylisoxazolyl | S | H | H | H | | | E |

TABLE I-continued

| Compound No. | W | A | X | Y | Z | Melting Point (°C.) | Olefinic* | Isomer+ |
|---|---|---|---|---|---|---|---|---|
| 85 | isoxazole (N-O) | S | H | H | H | | | E |
| 86 | isothiazole with methyl | S | H | H | H | | | E |
| 87 | isothiazole with methyl | S | H | H | H | | | E |
| 88 | isothiazole with methyl | S | H | H | H | | | E |
| 89 | oxazole with methyl | S | H | H | H | | | E |
| 90 | oxazole with methyl | S | H | H | H | | | E |
| 91 | oxazole with methyl | S | H | H | H | | | E |
| 92 | thiazole with methyl | S | H | H | H | | | E |
| 93 | thiazole with methyl | S | H | H | H | | | E |
| 94 | thiazole with methyl | S | H | H | H | | | E |
| 95 | N-methylimidazole with methyl | S | H | H | H | | | E |

TABLE I-continued

[Structure: W-A group on benzene ring with CO2CH3, =CH-OCH3, and X, Y, Z substituents]

| Compound No. | W | A | X | Y | Z | Melting Point (°C.) | Olefinic* | Isomer+ |
|---|---|---|---|---|---|---|---|---|
| 96 | 4-methyl-1-methylimidazol-5-yl | S | H | H | H | | | E |
| 97 | 1-methylimidazol-5-yl | S | H | H | H | | | E |
| 98 | benzo[d]isoxazol-3-yl | S | H | H | H | | | E |
| 99 | benzo[d]isothiazol-3-yl | S | H | H | H | | | E |
| 100 | 1-methyl-1H-indazol-3-yl | S | H | H | H | | | E |
| 101 | benzoxazol-2-yl | S | H | H | H | | | E |
| 102 | 5-chlorobenzoxazol-2-yl | S | H | H | H | | | E |
| 103 | 6-fluorobenzoxazol-2-yl | S | H | H | H | | | E |
| 104 | benzothiazol-2-yl | S | H | H | H | | | E |
| 105 | 5-fluorobenzothiazol-2-yl | S | H | H | H | | | E |
| 106 | 6-fluorobenzothiazol-2-yl | S | H | H | H | | | E |

TABLE I-continued

| Compound No. | W | A | X | Y | Z | Melting Point (°C.) | Olefinic* | Isomer+ |
|---|---|---|---|---|---|---|---|---|
| 107 | thiazolo[5,4-b]pyridin-2-yl (methyl) | S | H | H | H | | | E |
| 108 | 6-chloro-thiazolo[5,4-b]pyridin-2-yl (methyl) | S | H | H | H | | | E |
| 109 | 1-methyl-5-methyl-1,2,3-triazol-4-yl | S | H | H | H | | | E |
| 110 | 1-methyl-5-methyl-4,5-dihydro-1,2,3-triazol-4-yl | S | H | H | H | | | E |
| 111 | 1-methyl-1,2,4-triazol-5-yl | S | H | H | H | | | E |
| 112 | 1-methyl-3-methyl-1,2,4-triazol-5-yl | S | H | H | H | | | E |
| 113 | 1-methyl-5-methyl-tetrazol-? | S | H | H | H | | | E |
| 114 | 2-methyl-5-methyl-tetrazol-? | S | H | H | H | | | E |
| 115 | 5-trifluoromethyl-3-isopropyl-1,3,4-thiadiazol-2-yl | O | H | H | H | Oil | 7.56 | E |
| 116 | 6-chloro-2-methyl-benzoxazol-? | O | H | H | H | Oil | 7.53 | E |
| 117 | 5-fluoro-2-methyl-benzoxazol-? | O | H | H | H | 116–7 | 7.54 | E |

TABLE I-continued

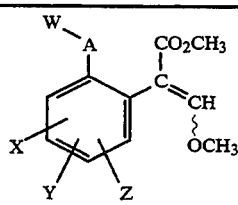

| Compound No. | W | A | X | Y | Z | Melting Point (°C.) | Olefinic* | Isomer+ |
|---|---|---|---|---|---|---|---|---|
| 118 | ![structure with N, NO2, S] | O | H | H | H | 94–5 | 7.58 | E |

*Chemical shift of singlet from olefinic proton on beta-methoxyacrylate group (ppm from tetramethylsilane). Solvent CDCl₃
+Geometry of beta-methoxyacrylate Table II shows selected proton nmr data for certain compounds described in Table I. Chemical shifts are measured in ppm from tetramethylsilane, and deuterochloroform was used as solvent throughout. The following abbreviations are used:

| br = broad | t = triplet |
| s = singlet | q = quartet |
| d = doublet | m = multiplet |
| J = coupling constant | Hz = Hertz |

TABLE II
SELECTED PROTON NMR DATA

| Compound No. | Proton nmr data |
|---|---|
| 115 | 3.64(3H, s); 3.77(3H, s); 7.37(4H, s); 7.56(1H, s). |
| 116 | 3.57(3H, s); 3.69(3H, s); 7.09–7.57(7H, m); 7.53(1H, s). |

The compounds of the invention having the general formula (I) can be prepared from substituted phenols or thiophenols of general formula (VII) by the steps shown in Scheme I. Throughout Scheme I the terms A, X, Y, Z and W are as defined above, and L is a halogen atom or another good leaving group.

Thus, compounds of general formula (I), which exist as geometric isomers which may be separated by chromatography, fractional crystallisation or distillation, can be prepared by O-methylation of compounds of general formula (III) using a base (such as potassium carbonate) and a methylating agent CH₃-L (II) in a suitable solvent (such as N,N-dimethylformamide) (Step (a) of Scheme I).

Compounds of general formula (III) can be prepared by treating phenylacetates of general formula (IV) with a base (such as sodium hydride) and a formic ester (such as methyl formate) in a suitable solvent (such as N,N-dimethyl formamide) (Step (b) of Scheme I).

Alternatively, compounds of general formula (I) can be prepared from acetals of general formula (XIII) by elimination of methanol under either acidic or basic conditions, at a suitable temperature and often in a suitable solvent (step (c) of Scheme I). Examples of reagents or reagent mixtures which can be used for this transformation are lithium di-isopropylamide; potassium hydrogen sulphate (see, for example, T Yamada, H Hagiwara and H Uda, J. Chem. Soc., Chemical Communications, 1980, 838, and references therein); and triethylamine, often in the presence of a Lewis acid such as titanium tetrachloride (see, for example, K Nsunda and L Heresi, J. Chem. Soc., Chemical Communications, 1985, 1000).

Acetals of general formula (XIII) can be prepared by treatment of methyl silyl ketene acetals of general formula (XIV) wherein R is an alkyl group with trimethyl orthoformate in the presence of Lewis acid such as titanium tetrachloride, at a suitable temperature and in a suitable solvent (see, for example, K Saigo, M Osaki and T Mukaiyama, Chemistry Letters, 1976, 769).

Methyl silyl ketene acetals of general formula (XIV) can be prepared from esters of general formula (IV) by treatement with a base and a trialkylsilyl halide of general formula R₃SiCl or R₃SiBr, such as trimethylsilyl chloride, or a base and a trialkylsilyl triflate of general formula R₃Si-OSO₂CF₃, in a suitable solvent and at a suitable temperature (see, for example, C Ainsworth, F Chen and Y Kuo, J. Organometallic Chemistry, 1972, 46, 59).

It is not always necessary to isolate the intermediates (XIII) and (XIV); under appropriate conditions, compounds of general formula (I) may be prepared from esters of general formula (IV) in "one pot" by the successive addition of suitable reagents listed above.

Compounds of general formula (IV) can be prepared by esterification of compounds of general formula (V) by standard methods described in the chemical literature (Step (d) of Scheme I).

Compounds of general formula (V) can be prepared by the reaction of compounds of general formula (VII) with compounds of formula (VI) in the presence of a base (such as potassium carbonate) and, if necessary, a transition metal or transition metal salt catalyst (such as copper-bronze) in a convenient solvent (such as N,N-dimethylformamide) (Step (e) of Scheme I).

Alternatively, compounds of general formula (IV) can be prepared from esters of general formula (VIII) by reaction with compounds of general formula (VI) in the presence of a base (such as potassium carbonate) and, if necessary, a transition metal or transition metal salt catalyst (such as copper-bronze) in a convenient solvent (such as N,N-dimethylformamide) (Step (f) of Scheme I).

Esters of general formula (VIII) can be prepared by esterification of compounds of general formula (VII) by standard methods described in the chemical literature (Step (g) of Scheme I).

Compounds of general formula (VII) can be prepared by standard methods described in the chemical literature. (For example, see, A. Clesse, W. Haefliger, D. Hauser, H. U. Gubler, B. Dewald and M. Baggiolini, *J.Med. Chem.*, 1981, 24, 1465).

Alternatively, compounds of the invention having the general formula (I) can be prepared from phenylacetates of general formula (XII) by the steps shown in Scheme II. Throughout Scheme II the terms A, W, X, Y, Z and L are as defined above, and M is a protecting group for a phenol or thiophenol group.

Thus compounds of general formula (I) can be prepared by reaction of compounds of general formula (IX) with compounds of general formula (VI) in the presence of a base (such as potassium carbonate) and, if necessary, a transition metal or transition metal salt catalyst in a convenient solvent (such as N,N-dimethylformamide) (step (h) of Scheme II).

Compounds of general formula (IX) can be prepared from protected phenol or thiophenol derivatives of general formula (X) by standard deprotection procedures as set out in the chemical literature (step (i) of Scheme II). For example, phenols of general formula (IX, A=O) can be prepared from benzyl ethers of general formula (X, A=O, M=CH$_2$Ph) by hydrogenolysis in the presence of a suitable catalyst (such as palladium supported on carbon).

Compounds of general formula (X), in which the group M is a standard phenol or thiophenol protecting group (such as benzyl), can be prepared by O-methylation of compounds of general formula (XI) using a base (such as potassium carbonate) and a methylating agent CH$_3$-L (II) in a suitable solvent (such as N,N-dimethylformamide) (step (j) of Scheme II).

Compounds of general formula (XI) can be prepared by treating phenylacetates of general formula (XII) with a base (such as sodium hydride) and a formic ester (such as methyl formate) in a suitable solvent (such as N,N-dimethylformamide) (step (k) of Scheme II).

Compounds of general formula (XII) can be prepared from compounds of general formula (VIII) by standard methods described in the chemical literature.

In further aspects the invention provides processes as herein described for preparing compounds of formula (I). It also provides the intermediate chemicals of formulae (III)–(V) and (XIII).

Scheme I

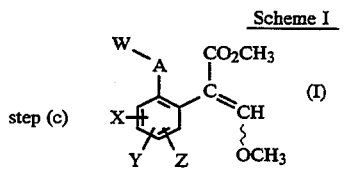

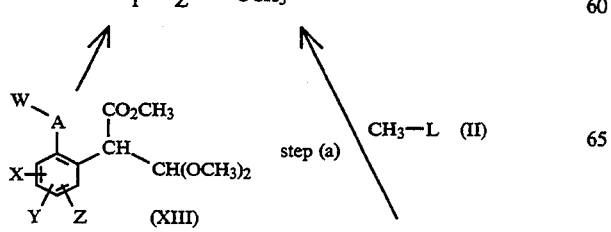

Scheme I

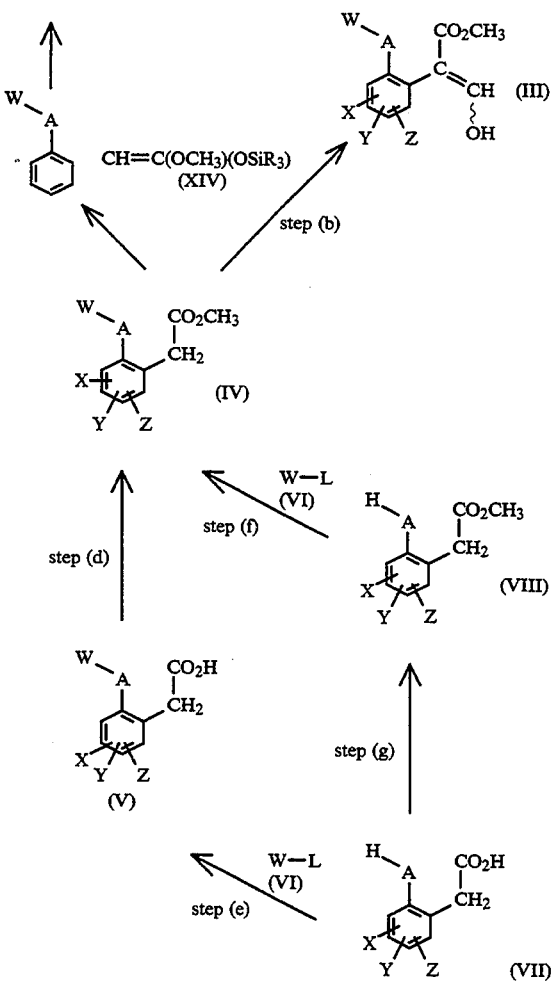

Scheme II

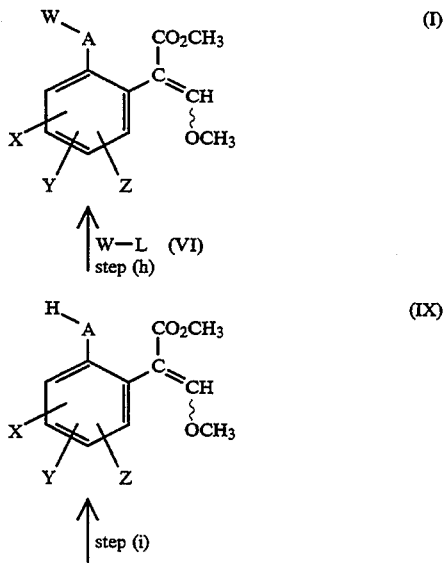

-continued
Scheme II

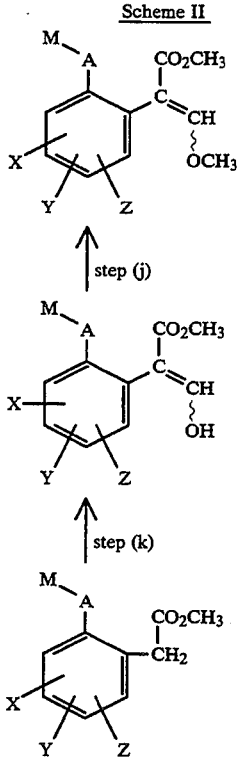

The compounds are active fungicides, and may be used to control one or more of the following pathogens:

Pyricularia oryzae on rice.

Puccinia recondita, Puccinia striiformis and other rusts on wheat, Puccinia hordei, Puccinia striiformis and other rusts on barley, and rusts on other hosts e.g. coffee, pears, apples, peanuts, vegetables and ornamental plants.

Erysiphe graminis (powdery mildew) on barley and wheat and other powdery mildews on various hosts such as Sphaerotheca macularis on hops, Sphaerotheca fuliginea on cucurbits (e.g. cucumber), Podosphaeraleucotricha on apples and Uncinulanecator on vines.

Helminthosporium spp., Rhynchosporium spp., Septoria spp., and Pseudocercosporella herpotrichoides.

Cercospora arachidicola and Cercosporidium personata on peanuts and other Cercospora species on other hosts for example sugar beet, bananas, soya beans and rice.

Botrytis cinerea (grey mould) on tomatoes, strawberries, vegetables, vines and other hosts.

Alternaria species on vegetables (e.g. cucumber), oil seed rape, apples, tomatoes and other hosts.

Venturia inaequalis (scab) on apples.

Plasmopara viticola on vines.

Other downy mildews such as Bremia lactucae on lettuce, Peronospora spp. on soybeans, tobacco, onions and other hosts and Pseudoperonospora humuli on hops and Pseudoperonospora cubensis on cucurbits.

Phytophthora infestans on potatoes and tomatoes and other Phytophthora spp. on vegetables, strawberries, avocado, pepper, ornamentals, tobacco, cocoa and other hosts.

Thanatephorus cucumeris on rice and other Rhizoctonia species on various host such as wheat and barley, vegetables, cotton and turf.

Some of the compounds show a broad range of activities against fungi in vitro. They may also have activity against various post-harvest diseases of fruit (e.g. Penicillium digitatum and italicum and Trichoderma viride on oranges, Gloesporium musarum on bananas) and Botrytis cinerea on grapes.

Further some of the compounds may be active as seed dressings against Fusarium spp., Septoria spp., Tilletia spp., (bunt, a seed borne disease of wheat), Ustilago spp., Helminthosporium spp. on cereals, Rhizoctonia solani on cotton and Pyricularia oryzae on rice.

The compounds can move acropetally in the plant tissue. Moreover, the compounds may be volatile enough to be active in the vapour phase against fungi on the plant.

The invention therefore provides a method of combating fungi, which comprises applying to a plant, to seed of a plant, or to the locus of the plant or seed, an effective amount of a fungicidal compound of formula (I).

The compounds may also be useful as industrial (as opposed to agricultural) fungicides, e.g. in the prevention of fungal attack on wood, hides, leather and especially paint films.

The compounds of the invention may have useful insecticidal activity against a range of insect species nematodes and mites. Therefore in a further aspect of the invention there is provided a method of killing or controlling insect, nematode or mite pests which comprises administering to the pest or to a locus thereof an effective amount of an insecticidal/nematocidal/miticidal compound of formula (I).

The compounds may be used directly for fungicidal or insecticidal purposes but are more conveniently formulated into compositions using a carrier or diluent. The invention thus provides fungicidal and insecticidal compositions comprising a compound of general formula (I) as hereinbefore defined, and a fungicidally/insecticidally acceptable carrier or diluent.

As fungicides, the compounds can be applied in a number of ways. For example they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules. Application can be to any part of the plant including the foliage, stems, branches or roots, or to soil surrounding the roots, or to the seed before it is planted; or to the soil generally, to paddy water or to hydroponic culture systems. The invention compounds may also be injected into plantsor sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example fillers such as kaolin, bentonite, kieselguhr, dolomite, calcium carbonate, talc, powdered magnesia, Fuller's earth, gypsum, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example a mineral oil) for assisting the adhesion of the composition to the seed; alternatively the active ingredient can be formulated for seed dressing purposes using an organic solvent (for example N-methylpyrrolidone, propylene glycol or dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone, and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent and including a suspending agent to stop the solid settling.

Compositions to be used as sprays may be in the form of aerosols wherein the formulation is held in a container under pressure in the presence of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in a micro-encapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants e.g. a wetting agent, dispersing agent, emulsifying agent or suspending agent. These agents can be cationic, anionic or non-ionic agents.

Suitable cationic agents are quaternary ammonium compounds, for example cetyltrimethylammonium bromide. Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which plant possess plant growth regulating, herbicidal or insecticidal activity.

A fungicidal compound which may be present in the composition of the invention may be one which is capable of combating ear diseases of cereals (e.g. wheat) such as Septoria, Gibberella and Helminthosporium spp., seed and soil-borne diseases and downy and powdery mildews on grapes and powdery mildew and scab on apple etc. By including another fungicide, the composition can have a broader spectrum of activity than the compound of general formula (I) alone. Further the other fungicide can have a synergisitic effect on the fungicidal activity of the compound of general formula (I). Examples of fungicidal compounds which may be included in the composition of the invention are carbendazim, benomyl, thiophanate-methyl, thiabendazole, fuberidazole, etridazole, dichlofluanid, cymoxanil, oxadixyl, ofurace, metalazyl, furalaxyl, benalaxyl, fosetyl-aluminium, fenarimol, iprodione, prothiocarb, procymidone, vinclozolin, penconazole, myclobutanil, propamocarb, R0151297, diniconazole, pyrazophos, ethirimol, ditalimfos, tridemorph, triforine, nuarimol, triazbutyl, guazatine, triacetate salt of 1,1'-iminodi-(octamethylene)diguanidine, buthiobate, propiconazole, prochloraz, flutriafol, hexaconazole, (2RS, 3RS)-2-(4-chlorophenyl)-3-cyclopropyl-1-(1H-1, 2,4-triazol-1-yl)butan-2-ol, (RS)-1-(4-chlorophenyl)-4,4-dimethyl-3-(1H-1,2,4-triazol-1-ylmethyl)pentan-3-ol, DPX H6573(1-(bis-4-fluorophenyl)methylsilyl)methyl)-1H-1,2,4-triazole, triadimefon, triademenol, diclobutrazol, fenpropimorph, pyrifenox, fenpropidin, chlorozolinate, imazalil, fenfuram, carboxin, oxycarboxin, methfuroxam, dodemorph, BAS 454, blasticidin S, kasugamycin, edifenphos, Kitazin P, cycloheximide, phthalide, probenazole, isoprothiolane, tricyclazole, 4-chloro-N-(cyano(ethoxy)methyl benzamide, pyroquilon, chlorbenzthiazone, neoasozin, polyoxin D, validamycin A, mepronil, flutolanil, pencycuron, diclomezine, phenazin oxide, nickel, dimethyldithiocarbamate, techlofthalam, bitertanol, bupirimate, etaconazole, hydroxyisoxazole, streptomycin, cyprofuram, biloxazol, quinomethionate, dimethirimol, 1-(2-cyano-2-methoxyiminoacetyl)-3-ethyl urea, fenapanil, tolclofosmethyl, pyroxyfur, polyram, maneb, mancozeb, captafol, chlorothalonil, anilazine, thiram, captan, folpet, zineb, propineb, sulphur, dinocap, dichlone, chloroneb, binapacryl, nitrothalisopropyl, dodine, dithianon, fentin hydroxide, fentin acetate, tecnazene, quintozene, dicloran, copper containing compounds such as copper oxychloride, copper sulphate and Bordeaux mixture, and organomercury compounds.

The compounds of general formula (I) can be mixed with soil, peat or other rooting media for the protection of plants against seed-borne, soil-borne or foliar fungal diseases.

Suitable insecticides which may be incorporated in the composition of the invention include pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, monocrotophas, buprofezin, ethroproxyfen and cycloprothrin.

Plant growth regulating compounds are compounds which control weeds or seedhead formation, or selectively control the growth of less desirable plants (e.g. grasses).

Examples of suitable plant growth regulating compounds for use with the invention compounds are the gibberellins (e.g. $GA_3$, $GA_4$ or $GA_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acid (e.g. triiodobenzoic acid), morphactins (e.g. chlorfluoroecol), maleic hydrazide, glyphosate, glyphosine, long chain fatty alcohols and acids, dikegulac, paclobutrazol, fluoridamid, mefluidide, substituted quaternary ammonium and phosphonium compounds (e.g. chloromequat chlorphonium or mepiquatchloride), ethephon, carbetamide, methyl-3,6-dichloroanisate, daminozide, asulam, abscisic acid, isopyrimol, 1-(4-chlorophenyl)-4,6-dimethyl-2-oxo-1,2-dihydropyridine-3-carboxylic acid, hydroxybenzonitriles (e.g. bromoxynil), difenzoquat, benzoylprop-ethyl 3,6-dichloropicolinic acid, fenpentezol, inabenfide, triapenthenol and tecnazene.

The following Examples illustrate the invention. Throughout these Examples, the term 'ether' refers to diethyl ether; chromatography was carried out using silica gel as the solid phase; magnesium sulphate was used to dry solutions; and reactions involving water- or air-sensitive intermediates were performed under atmospheres of nitrogen. Temperatures are expressed in degrees centigrade.

Where shown, infrared and nmr data are selective; no attempt is made to list every absorption. The following abbreviations are used throughout:

| | |
|---|---|
| DMF = N,N-dimethylformamide | delta = chemical shift |
| g = gramme(s) | $CDCl_3$ = deuterochloro- |

-continued

| | | | |
|---|---|---|---|
| mmol = | millimole(s) | | form |
| ml = | milliter(s) | s = | singlet |
| mmHg = | millimeters pressure of mercury | d = | doublet |
| | | t = | triplet |
| M.P. = | melting point | br = | broad |
| nmr = | nuclear magnetic resonance | | |

EXAMPLE 1

This Example illustrates the preparation of E-methyl 3-methoxy-2-[2'-(benzoxazol-2''-yloxyphenyl)]propenoate (Compound No. 44 of Table I).

2-Hydroxyphenylacetic acid (50 g) was added to a solution of hydrogen chloride in methanol [prepared from acetyl chloride (25 ml) and methanol (250 ml)]. The solution was stirred at room temperature for three hours and then allowed to stand overnight (fifteen hours). The resulting mixture was concentrated under reduced pressure, and the residue was taken up in ether (250 ml) and washed with an aqueous solution of sodium bicarbonate until effervescence ceased. The ethereal solution was dried and then concentrated under reduced pressure and the resulting solid was recrystalized from ether/petrol to afford methyl 2-hydroxyphenylacetate (50 g; 92% yield) as white, powdery crystals, M.P. 70°–72° C.; infrared maxima (nujol mull): 3420, 1715 $cm^{-1}$; $^1H$ nmr ($CDCl_3$, 90 MHz): delta 3.70 (2H, s), 3.75 (3H,s), 6.80–6.95 (2H,m), 7.05–7.10 (1H,m), 7.15–7.25 (1H,m), 7.40 (1H,s)ppm.

Methyl 2-hydroxyphenylacetate (21.0 g) was dissolved in dry DMF (200 ml), and dry potassium carbonate (19.35 g) was added in one portion. Benzyl bromide (23.94 g) in dry DMF (50 ml) was added dropwise to this mixture, with stirring, at room temperature. After eighteen hours the mixture was poured into water (500 ml) and extracted with ether (2×400 ml). The extracts were washed with water (3×150 ml) and brine (100 ml), dried and filtered through silica gel (50 g; Merck 60), then concentrated under reduced pressure to afford a yellow oil. Distillation at 160° C. and 0.05 mmHg afforded methyl 2-benzyloxyphenylacetate as a clear, colourless oil (26.99 g; 83% yield), infrared maximum (film): 1730 $cm^{-1}$; $^1H$ nmr ($CDCl_3$, 90 MHz): delta 3.60 (3H,s), 3.75 (2H,s), 4.10 (2H,s), 6.80–7.40 (9H,m).

Methyl 2-benzyloxyphenylacetate (26.99 g) and methyl formate (126.62 g) in dry DMF (300 ml) were added dropwise to a stirred suspension of sodium hydride (50% disp. in oil, 10.13 g) in DMF (300 ml) at 0° C. After stirring at 0° C. for two hours the mixture was poured into water (1000 ml) and washed with ether (2×150 ml). The aqueous layer was acidified to pH4 with 6M hydrochloric acid then extracted with ether (2×350 ml). The extracts were dried and concentrated under reduced pressure to afford crude methyl 3-hydroxy-2-[2'-benzyloxyphenyl]propenoate as a yellow oil, infrared maxima (film): 1720, 1660 $cm^{-1}$.

The crude methyl 3-hydroxy-2-(2'-benzyloxyphenyl)propenoate was dissolved in dry DMF (100 ml) and potassium carbonate (29.0 g) was added in one portion. Dimethyl sulphate (16.00 g) in dry DMF (10 ml) was then added dropwise with stirring. After ninety minutes, water (300 ml) was added and the solution was extracted with ether (2×300 ml). After washing with water (3×150 ml) and brine, the extracts were dried and concentrated under reduced pressure, and the resulting yellow oil solidified on trituration with ether/- petrol. Recrystallization from dry methanol afforded E-methyl 3-methoxy-2-(2'-benzyloxyphenyl)propenoate as a white, crystalline solid (5.44 g, 17% yield from methyl 2-benzyloxyphenylacetate), M.P. 76°–77° C.; infrared maxima (nujol mull): 1710, 1640 cm$^{-1}$; $^1$H nmr (CDCl$_3$, 90 MHz): delta 3.63 (3H, s), 3.75 (3H, s), 5.05 (2H, s), 6.80–7.40 (9H,m), 7.50 (1H,s)ppm.

E-methyl 3-methoxy (2'-benzyloxyphenyl)propenoate (5.44 g) was dissolved in ethyl acetate (50 ml) and 5% palladium on carbon (0.25 g) was added. The stirred mixture was hydrogenated at three atmospheres pressure, with stirring, until no more hydrogen was taken up, then filtered through celite and silica gel (50 g, Merck 60). Concentration of the filtrate under reduced pressure afforded E-methyl 3-methoxy-2-(2'-hydroxyphenyl)propenoate as a white crystalline solid (3.76 g; 99% yield), M.P. 125°–126° C.; infrared maxima (nujol mull): 3400, 1670 cm$^{-1}$; $^1$H nmr (CDCl$_3$, 270 MHz): delta 3.80 (3H, s), 3.90 (3H, s), 6.20 (1H,s), 6.80–7.00 (2H,m), 7.10–7.30 (2H,m), 7.60 (1H,s)ppm.

E-methyl 3-methoxy-2-(2'-hydroxyphenyl)propenoate (0.5 g), potassium carbonate (0.24 g) and 2-chlorobenzoxazole (5 ml) were stirred in dry DMF (5 ml) for two hours at room temperature. Water (25 ml) was added and the solution was extracted with ether (2×50 ml). The ether extracts were washed with water (2×25 ml) and brine (25 ml) and then dried and concentrated under reduced pressure. Chromatography of the residue on silica gel (Merck 60) using ether afforded the title compound as a clear, colourless oil (0.45 g; 58% yield), $^1$H nmr (CDCl$_3$, 270 MHz): delta 3.80 (3H,s), 3.95 (3H,s), 7.40–7.80 (8H,m), 7.80 (1H,s). $^{13}$C nmr (CDCl$_3$) showed decoupled signals at delta 167.21, 161.99, 160.69, 150.35, 148.31, 140.85, 132.47, 129.07, 126.00, 124.79, 124.30, 123.06, 120.90, 118.54, 109.64, 106.42, 61.87, and 51.49 ppm.

The following are examples of compositions suitable for agricultural and horticultural purposes which can be formulated from the compounds of the invention. Such compositions form another aspect of the invention. Temperatures are given in degrees centigrade (°C.): percentages are by weight.

EXAMPLE 2

This Example illustrates the preparation of E-methyl 3-methoxy-2-[2'-(thiazolylpyrid-2"-yloxyphenyl)]-propenoate (Compound No. 50 of Table I).

To a stirred solution of E-methyl 3-methoxy-2-(2'-hydroxyphenyl)propenoate (0.40 g) and 2-chlorothiazolopyridine (1.30 g) in dry DMF (10 ml) at 0° C. was added potassium carbonate (0.53 g). The reaction mixture was allowed to reach room temperature over a period of 2 days and then partitioned between water and ether. The ether layer was dried, filtered and evaporated. The residue was chromatographed (eluent ether-hexane mixtures) to afford the title compound as an oil (0.16 g) which crystallised on trituration with ether-hexane. Recrystallisation from ether-hexane gave a pale yellow solid (0.10 g), 15.4% m.p. 109°–111° C.

EXAMPLE 3

This Example illustrates the preparation of E-methyl 3-methoxy-2-[2'-(5"-trifluoromethyl-1",3",4"-thiadiazol-2"-yloxyphenyl)]propenoate (Compound No. 115 of Table I).

E-Methyl 3-methoxy-2-(2"-hydroxyphenyl)propenoate (1.00 g) was treated with 2-bromo-5-trifluoromethyl-1,3,4-thiadiazole (4.48 g) and potassium carbonate (1.33 g) in dry DMF (15 mls) as described in Example 2. The crude product obtained after work up as a pale brown liquid (2.30 g) was chromatographed (eluent ether-hexane 3:2) to afford the title compound as a colourless oil (1.25 g, 72%), $^1$H nmr (CDCl$_3$) delta 3.04 (3H, s); 3.77 (3H, s); 7.37 (4H, s); 7.56 (1H, s); (Microanalysis found C 46.96%, H 3.27%, N 7.78%; C$_{14}$H$_{11}$F$_3$N$_2$O$_4$S requires C 46.67%, H 3.05%, N 7.78%).

EXAMPLE 4

This Example illustrates the preparation of E-methyl 3-methoxy-2-[2'-(5'-nitrothiazol-2'-yloxyphenyl)]-propenoate (Compound No. 118 of Table I).

E-Methyl 3-methoxy-2-(2'-hydroxyphenyl)propenoate (1.00 g) was treated with 2-bromo-5-nitrothiazole (2.00 g) and potassium carbonate (1.99 g) in dry DMF (10 mls) as described in Example 2. The crude product was obtained on work up as a brown oil which partially crystallised on standing. Chromatography (eluent ether-hexane 2:1) afforded the title compound as a yellow oil (1.17 g) which crystallised on trituration with ether-hexane. Recrystallisation from hexane-dichloromethane yielded a light yellow crystalline solid (0.76 g, 47%)m.p. 94-5° C.

EXAMPLE 5

An emulsifiable concentrate is made up by mixing and stirring the ingredients until all are dissolved.

| | |
|---|---|
| Compound No. 44 of Table I | 10% |
| Benzyl alcohol | 30% |
| Calcium dodecylbenzenesulphonate | 5% |
| Nonylphenolethoxylate (13 moles ethylene oxide) | 10% |
| Alkyl benzenes | 45% |

EXAMPLE 6

The active ingredient is dissolved in methylene dichloride and the resultant liquid sprayed on to the granules of attapulgite clay. The solvent is then allowed to evaporate to produce a granular composition.

| | |
|---|---|
| Compound No. 44 of Table I | 5% |
| Attapulgite granules | 95% |

EXAMPLE 7

A composition suitable for use as a seed dressing is prepared by grinding and mixing the three ingredients.

| | |
|---|---|
| Compound No. 44 of Table I | 50% |
| Mineral oil | 2% |
| China clay | 48% |

EXAMPLE 8

A dustable powder is prepared by grinding and mixing the active ingredient with talc.

| | |
|---|---|
| Compound No. 44 of Table I | 5% |
| Talc | 95% |

EXAMPLE 9

A suspension concentrate is prepared by ball milling the ingredients to form an aqueous suspension of the ground mixture with water.

| | |
|---|---|
| Compound No. 44 of Table I | 40% |
| Sodium lignosulphonate | 10% |
| Bentonite clay | 1% |
| Water | 49% |

This formulation can be used as a spray by diluting into water or applied directly to seed.

EXAMPLE 10

A wettable powder formulation is made by mixing together and grinding the ingredients until all are thoroughly mixed.

| | |
|---|---|
| Compound No. 44 of Table I | 25% |
| Sodium lauryl sulphate | 2% |
| Sodium lignosulphonate | 5% |
| Silica | 25% |
| China clay | 43% |

EXAMPLE 11

The compounds were tested against a variety of foliar fungal diseases of plants. The technique employed was as follows.

The plants were grown in John Innes Potting Compost (No. 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed onto the foliage and applied to the roots of the plants in the soil. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on Erisiphe graminis in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4=no disease
3=trace −5% of disease on untreated plants
2=6–25% of disease on untreated plants
1=26–59% of disease on untreated plants
0=60–100% of disease on untreated plants The results are shown in Table III.

TABLE III

| COMPOUND NUMBER (TABLE I) | PUCCINIA RECONDITA (WHEAT) | ERYSIPHE GRAMINIS (BARLEY) | VENTURIA INAEQUALIS (APPLE) | PYRICULARIA ORYZAE (RICE) | CERCOSPORA ARACHIDICOLA (PEANUTS) | PLASMOPARA VITICOLA (VINES) | PHYTOPHTHORA INFESTANS (TOMATO) |
|---|---|---|---|---|---|---|---|
| 44 | 4 | 4 | 4 | 4 | 4 | 4 | 4 |
| 45 | 3 | 3 | 1 | 0 | 0 | 4 | 2 |
| 46 | 4 | 4 | 4 | — | 4 | 4 | 4 |
| 50 | 4 | 4 | 4 | 4 | 4 | 4 | 4 |
| 51 | 4 | 0 | 4 | 3 | 4 | 4 | 0 |
| 115 | 4 | 4 | 4 | 0 | 0 | 4 | 4 |
| 116 | 4 | 4 | 4 | 3 | 4 | 4 | 4 |
| 117 | 4 | 4 | 4 | 3 | 4 | 4 | 4 |

EXAMPLE 12

This Example illustrates the insecticidal properties of the compound 44 in Table I.

The activity of the compound was determined using insect, mite and nematode pests. The compound was used in the form of a liquid preparation containing 500 parts per million (ppm) by weight of the compound. The preparation was made by dissolving the compound in acetone and diluting the solution with water containing 0.1% by weight of a wetting agent sold under the trade name "SYNPERONIC" NX until the liquid preparation contained the required concentration of the product. "SYNPERONIC" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparation. The mortality of the pests was then assessed at periods usually varying from one to seven days after the treatment.

The results of the tests are given in Table V as a grading of mortality designated as 9, 5 or 0 wherein 9 indicates 80–100% mortality, 5 indicates 50–79% mortality and 0 indicates less than 50% mortality.

In Table V the pest organism used is designated by a letter code and the pest species, the support medium or food, and the type and duration of test is given in Table IV.

The knockdown properties of compound 44 in Table I against Musca domestica was demonstrated as follows.

A sample of compound 44 was diluted with 2 mls acetone and made up of a 2000 ppm solution with 0.1% aqueous synperonic solution. The solution (1 ml) was then sprayed directly onto twenty mixed sex houseflies held in a drinking cup. Immediately after spraying the cups were inverted and left to dry. An assessment of knockdown was made when the cups were righted 15 minutes later. The flies were then provided with a 10% sucrose solution on a cotton wool pad, and held for 48 hours in a holding room conditioned at 25° C. and 65% relative humidity before a mortality assessment was made.

TABLE IV

| CODE LETTERS | TEST SPECIES | SUPPORT MEDIUM/FOOD | TYPE OF TEST | DURATION (DAYS) |
|---|---|---|---|---|
| TU$_A$ | Tetranychus urticae (spider mites - adults) | French bean leaf | Contact | 3 |
| DB | Diabrotica balteata (rootworm larvae) | Filter paper/ maize seed | Residual | 3 |
| MD$_C$ | Musca domestica (houseflies - adults) | Cotton wool/ sugar | Contact | 1 |
| MD$_K$ | Musca domestica (houseflies - adults) | Inverted cup | Knockdown | 2 |
| SP | Spodoptera exigua (lesser army worm - larvae) | Cotton leaf | Residual | 3 |

"Contact" test indicates that both pests and medium were treated and "residual" indicates that the medium was treated before infestation with the pests.

TABLE V

| COMPOUND NUMBER (TABLE I) | RATE (PPM) | TU$_A$ | MD$_C$ | MD$_K$ | SP | DB |
|---|---|---|---|---|---|---|
| 44 | 500 | 9 | 0 | 0 | 9 | 9 |

We claim:

1. A compound having the general formula (I):

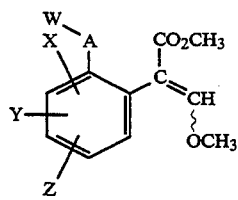

and stereoisomers thereof, wherein X, Y and Z, which are the same or different, are hydrogen; halogen; hydroxy; $C_{1-6}$ alkyl or $C_{1-6}$ alkyl substituted by hydroxy, halogen, $C_{1-4}$ alkoxy or $C_{1-4}$ alkoxycarbonyl; $C_{2-6}$ alkenyl or $C_{2-6}$ alkenyl substituted by, phenyl or a 5- or 6-membered heteroaromatic selected from the group consisting of furyl, thienyl or pyridyl; $C_{2-6}$ alkenyl wherein the terminal carbon atom of the alkenyl group forms part of a 5- or 6-membered cycloalkyl ring; phenyl; $C_{2-6}$ alkynyl or $C_{2-6}$ alkynyl substituted with phenyl; $C_{1-6}$ alkoxy or $C_{1-6}$ alkoxy substituted by hydroxy, halogen, $C_{1-4}$ alkoxy or $C_{1-4}$ alkoxycarbonyl; phenoxy; phenyl-($C_{1-6}$) alkyl and phenyl($C_{1-6}$) alkoxy whose alkyl moieties are unsubstituted or substituted by hydroxy or $C_{1-4}$ alkoxy; phenoxy($C_{1-6}$)alkyl whose alkyl moiety is unsubstituted or substituted by methoxy; —OCOCH$_3$, —NR$^1$R$^2$; —NR$^3$COR$^4$; nitro; cyano; —CO$_2$R$^5$; —CONR$^6$R$^7$ or —COR$^8$;

A is an oxygen or sulphur atom; R$^5$, R$^6$, R$^7$ and R$^8$, which are the same or different, are hydrogen, $C_{1-6}$ alkyl, $C_{3-6}$ cycloalkyl, $C_{3-6}$ cycloalkyl($C_{1-6}$)alkyl, $C_{2-6}$ alkenyl, $C_{2-6}$ alkynyl, phenyl or phenyl($C_{1-6}$)alkyl whose alkyl moiety is unsubstituted or substituted with hydroxy or $C_{1-4}$ alkoxy; any of the foregoing phenyl and heteroaromatic groups being unsubstituted or substituted by halogen hydroxy, $C_{1-4}$ alkyl, $C_{1-4}$ alkoxy, trifluoromethyl, trifluoromethoxy, phenoxy, benzyloxy, nitro, amino, phenyl, carboxy, cyano, alkylcarbonylamino and methylenedioxy; and wherein the phenoxy and benzyloxy groups are unsubstituted or substituted by halogen, hydroxy, $C_{1-4}$ alkyl, $C_{1-4}$ alkoxy, trifluoromethyl, trifluoromethoxy, nitro, amino, phenyl, carboxy, a carboxylic acid ester, cyano, alkylcarbonylamino and methylenedioxy; R$^1$ and R$^2$ which are the same or different are hydrogen, $C_{1-6}$ alkyl or phenyl; R$^3$ is hydrogen or $C_{1-6}$ alkyl, R$^4$ is phenyl, furyl or thienyl; and W is C-linked five membered heterocycle containing 1-4 atoms independently selected from the group consisting of nitrogen, sulphur and oxygen; the W heterocycle being unsubstituted or substituted by a substituent selected from the group consisting of halogen, nitro, unsubstituted $C_{1-4}$ alkyl, $C_{1-4}$ alkyl substituted with halogen, hydroxy or $C_{1-4}$ alkoxy, unsubstituted $C_{1-4}$ alkoxy or $C_{1-4}$ alkoxy substituted by halogen, hydroxy or $C_{1-4}$ alkoxy; unsubstituted phenoxy or phenoxy substituted with halogen, hydroxy, unsubstituted amino or amino substituted with $C_{1-4}$ alkyl, and cyano; or two adjacent substituents on W together form a fused benzene or pyridine ring which is unsubstituted or substituted with substituents selected from the group recited for W; and metal complexes thereof.

2. A compound according to claim 1 which is in the form of the (E)-isomer.

3. A compound according to claim 1 in which W is a group of the formula (A):

in which D is oxygen or sulphur; E is nitrogen or C-J and G and J are independently hydrogen, halogen, hydroxy, $C_{1-4}$ alkyl, $C_{1-4}$ alkoxy, halo($C_{1-4}$)alkyl, halo($C_{1-4}$)alkoxy, phenoxy, nitro, amino or mono- or di-($C_{1-4}$)-alkylamino; or G and J join to form a fused benzene or pyridine ring which is optionally substituted by halogen, hydroxy, $C_{1-4}$ alkyl, $C_{1-4}$ alkoxy, halo($C_{1-4}$)alkyl, halo($C_{1-4}$)alkoxy, phenoxy, nitro, amino or mono- or di-$C_{1-4}$)alkylamino.

4. A compound according to claim 1 in which X, Y and Z are all hydrogen.

5. A compound according to claim 1 wherein W is

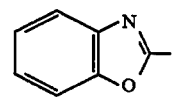

A is O and X, Y and Z are each hydrogen.

6. A pesticidal composition comprising, as an active ingredient, an effective amount of a compound as claimed in claim 1 together with a pesticidal carrier or diluent therefor.

7. A method of combating fungi which comprises applying to a plant, to seed of a plant, or to a locus of the plant or seed, an effective amount of a compound as claimed in claim 1.

8. A method of killing or controlling insect, nematode or mite pests which comprises administering to the pest or a locus thereof an effective amount of a pesticidal compound as claimed in claim 1.

* * * * *